(12) United States Patent
Andres et al.

(10) Patent No.: US 9,403,163 B2
(45) Date of Patent: Aug. 2, 2016

(54) ELECTRIC PIPETTING APPARATUS, AND METHOD FOR OPERATING AN ELECTRIC PIPETTING APPARATUS

(71) Applicant: Eppendorf AG, Hamburg (DE)

(72) Inventors: Karl-Friedrich Andres, Bargteheide (DE); Janine Jacobi, Hamburg (DE); Peter Molitor, Hamburg (DE); Peter Schmidt, Luebeck (DE)

(73) Assignee: EPPENDORF AG, Hamburg (DE)

( * ) Notice: Subject to any disclaimer, the term of this patent is extended or adjusted under 35 U.S.C. 154(b) by 0 days.

(21) Appl. No.: 13/847,941

(22) Filed: Mar. 20, 2013

(65) Prior Publication Data

US 2013/0288382 A1    Oct. 31, 2013

Related U.S. Application Data

(60) Provisional application No. 61/613,020, filed on Mar. 20, 2012, provisional application No. 61/613,537, filed on Mar. 21, 2012.

(30) Foreign Application Priority Data

Mar. 20, 2012  (EP) .................. 12 001 933

(51) Int. Cl.
*B01L 3/02* (2006.01)
*G01N 35/10* (2006.01)

(52) U.S. Cl.
CPC ............ *B01L 3/021* (2013.01); *B01L 3/0237* (2013.01); *B01L 2200/087* (2013.01); *B01L 2200/14* (2013.01); *B01L 2300/024* (2013.01); *B01L 2300/027* (2013.01); *G01N 2035/1039* (2013.01); *Y10T 436/2575* (2015.01)

(58) Field of Classification Search
CPC ...................................... B01L 3/021
USPC ..................... 73/864.01; 436/180
See application file for complete search history.

(56) References Cited

U.S. PATENT DOCUMENTS

| 2005/0118069 A1* | 6/2005 | Solotareff et al. | ............ 422/100 |
| 2009/0000402 A1* | 1/2009 | Magnussen et al. | ....... 73/864.18 |

(Continued)

FOREIGN PATENT DOCUMENTS

| EP | 1 859 869 A1 | 11/2007 |
| EP | 1 878 500 A1 | 1/2008 |

(Continued)

OTHER PUBLICATIONS

"Automatic" was accessed on Sep. 3, 2014 via the site http://dictionary.reference.com/browse/automatically.*

*Primary Examiner* — Lyle Alexander
*Assistant Examiner* — Emily Berkeley
(74) *Attorney, Agent, or Firm* — Arnold & Porter LLP; Todd A. Lorenz (57) ABSTRACT

The invention relates to a pipetting apparatus, for pipetting a fluid sample in accordance with at least one mode of operation of the pipetting apparatus, which is controlled by an operating parameter set, which is associated with a corresponding mode of operation, wherein the electric control device of the pipetting apparatus is designed to automatically store the at least one parameter value set determined by the user to be the at least one historic parameter value set for this mode of operation in the memory device, and is designed to provide, after the operating parameter set for this mode of operation has changed, the at least one automatically stored historic parameter value set for this mode of operation again for the subsequent control of the at least one, same, pipetting process. The invention also relates to a method for operating the pipetting apparatus.

16 Claims, 4 Drawing Sheets

(56) References Cited

U.S. PATENT DOCUMENTS

2009/0074622 A1* 3/2009 Kalamakis ............ B01L 3/0217
422/400
2013/0013875 A1   1/2013 Brown et al.

FOREIGN PATENT DOCUMENTS

| WO | WO 00/51739 A1 | 9/2000 |
| WO | WO 2005/079988 A1 | 9/2005 |

* cited by examiner

ELECTRIC PIPETTING APPARATUS, AND METHOD FOR OPERATING AN ELECTRIC PIPETTING APPARATUS

The invention relates to an electric pipetting apparatus and to a method for operating an electric pipetting apparatus.

Such pipetting apparatuses are usually used in medical, biological, biochemical, chemical and other laboratories. They are used in the laboratory for transporting and transferring fluid samples having small volumes, particularly for the precise metering of the samples. In pipetting apparatuses, liquid samples, for example, are aspirated by means of underpressure into pipette containers, e.g. pipette tips, are stored there and are delivered from them again at the destination. An electric pipetting apparatus uses at least one electrical operating parameter which at least influences or controls the operation of the pipetting apparatus. Electric pipetting apparatuses are subsequently also referred to by the term "pipetting apparatuses" for short.

The pipetting apparatuses include hand-held pipettes and dispensers, for example. A pipette is understood to mean an appliance in which a movement device which is associated with the appliance and which may have a piston, in particular, can be used to aspirate a sample to be pipetted into a pipetting container that is connected to the pipette. In the case of an air-cushion pipette, the piston is associated with the appliance, and the sample to be pipetted and the end of the piston have an air cushion between them which, when the sample is admitted into the pipetting container, is under an underpressure which aspirates the sample into the pipetting container. A dispenser is understood to mean an appliance in which a movement device, which may have a piston, in particular, can be used to aspirate a volume to be pipetted into a pipetting container that is connected to the dispenser, the movement device being at least partially associated with the pipetting container, for example by virtue of the piston being arranged in the pipetting container. In the case of the dispenser, the end of the piston is very close to the sample to be pipetted or is in contact therewith, for which reason the dispenser is also referred to as a direct displacement pipette.

In the case of a pipetting apparatus, the quantity of sample delivered by a single operating action can correspond to the quantity of sample aspirated into the appliance. Alternatively, provision may be made for an admitted quantity of sample which corresponds to a plurality of delivery quantities to be delivered again in steps. In addition, a distinction is drawn between single channel pipetting apparatuses and multichannel pipetting apparatuses, with single-channel pipetting apparatuses containing only a single delivery/admission channel, and multichannel pipetting apparatuses containing a plurality of delivery/admission channels which allow a plurality of samples to be delivered or admitted in parallel, in particular. Pipetting apparatuses may be manually operated, in particular, i.e. can imply that the driving of the movement device is produced by the user, and/or may be electrically operated, in particular. Even in the case of manual operation of the movement device, a pipetting apparatus may be an electric pipetting apparatus, for example by virtue of the current delivery volume or at least another operating parameter being selected electrically.

An example of a hand-held, electronic pipette is the Eppendorf XPLORER® from Eppendorf AG, Germany, Hamburg; examples of hand-held electronic dispensers are the MULTIPLETTE STREAM® and MYLTIPIPETTE XSTREAM® from Eppendorf AG, Germany, Hamburg.

Electric pipetting apparatuses afford numerous advantages over non-electric pipetting apparatuses, since a multiplicity of functions can easily be implemented. In particular, electric pipetting apparatuses allow the performance of particular, program-controlled pipetting processes to be simplified by virtue of these being automated or semi-automated. Typical operating parameters for controlling such pipetting processes using appropriate pipetting programs relate to the volume for aspirating or delivering liquid, the order and repetitions thereof, and possibly temporal parameters for the temporal distribution of these processes.

An electric pipetting apparatus may be designed to be operated in one mode of operation or in a plurality of modes of operation. A mode of operation may provide for a set containing one or more operating parameters for the pipetting apparatus which influence or control a pipetting process of the pipetting apparatus to be automatically requested, selected and/or applied. The decision regarding how the value of an operating parameter is meant to be usually needs to be made by the user in each case when using the pipetting apparatus, and the operating parameter needs to be stipulated accordingly. Depending on the required number of operating parameters, stipulation of the operating parameters takes time for the user. In particular, this stipulation of the operating parameters is repeated if a pipetting process which has previously had its parameter values selected needs to be performed again with different operating parameters when another operating process has been performed in the meantime, which means that the same operating parameters need to be stipulated again. An approach to solving the problem in the case of known programmable, electric pipetting apparatuses involves a set of operating parameter values being able to be preprogrammed by the user in each case, being able to be stored by the user in the pipetting apparatus under a particular name and possibly by performing further editing steps, and being able to be loaded by the user under this name as required in order to operate a pipetting process using this parameter value set. Such a procedure requires relatively precise planning of the desired work processes.

It is an object of the present invention to provide an electric pipetting apparatus and a method for operating an electric pipetting apparatus which the user can use conveniently.

The invention achieves this object by means of the pipetting apparatus according to Claim 1 and the method according to Claim 14. Preferred refinements are covered by the subclaims, in particular.

The pipetting apparatus according to the invention, for performing an at least partially electrically controlled pipetting process on at least one fluid laboratory sample in accordance with at least one mode of operation of the pipetting apparatus, has:

an electric control device (17) for controlling the pipetting process, said control device being able to be controlled by an operating parameter set which is able to be stipulated by a user and which is associated with a mode of operation and respectively comprises at least one operating parameter, wherein the user stipulates the operating parameter by selecting the desired value of the operating parameter as a parameter value and in this way determining a parameter value set having at least one parameter value, wherein this parameter value set allows the parameter-based program function of this mode of operation to be used, in particular, at least one operator control device (12, 13, 14a, 14b) for the stipulation of the operating parameter set by the user, an electric memory device (18) for storing the at least one parameter value set, wherein the electric control device (17) is designed to automatically store the at least one parameter value set determined by the user as the at least one historic parameter value set for this mode of operation in the memory device (18), and, in particular, is designed to provide again, after the operating parameter set for this mode of operation has changed, the at least one automatically stored historic parameter value set for this mode of operation for the subsequent control of the at least one, same, pipetting process.

The pipetting apparatus according to the invention affords the advantage that at least one parameter value set which has already been stipulated, and particularly used, by the user previously in the operating history of the pipetting apparatus does not need to be stipulated again if the history function of the pipetting apparatus is active, in particular is activated. In this way, the user can dispense with numerous editing processes in the pipetting apparatus in the course of time. The pipetting apparatus according to the invention is therefore more convenient to use. This applies all the more as the editing processes do not just necessitate numerous additional interactions between the user and the pipetting apparatus but also require more complex, often not very intuitive, interactions which are relatively inconvenient and susceptible to error. The use of the pipetting apparatus according to the invention is therefore also safer.

The function of the automatic storage of the historic parameter value set, namely that the electric control device is designed to automatically store the at least one parameter value set determined by the user, and associated with the operating parameter set for a mode of operation, as at least one historic parameter value set for this mode of operation in the memory device, is also called a history function. Preferably, the pipetting apparatus and/or the control device is/are designed to allow the function of the automatic storage of the historic parameter value set to be either activated and/or deactivated by the user. This can be accomplished by means of a switching element on the operator control device, and/or by means of setting a software variable or an operating parameter for the pipetting apparatus.

In the present case, a parameter value denotes the specific value which an operating parameter adopts on the basis of the stipulation by the user or as a result of other stipulation.

The memory device is preferably a memory area section, which can be addressed by the control device and which is defined particularly by software, in a larger memory area. The memory area section may be a file. The memory area may be a data memory. A memory area may be a non-physical storage space which is managed by software and which is physically arranged in a hardware memory. The memory device may have a hardware memory. The hardware memory is preferably a permanent data memory, preferably a FLASH memory. The hardware memory is preferably designed to be able to perform preferably at least 100 000, preferably at least 150 000 or preferably at least 300 000 write cycles or erase cycles.

The pipetting apparatus according to the invention is preferably designed to be used to perform at least one pipetting process in accordance with at least one mode of operation of the pipetting apparatus. In particular, the pipetting apparatus according to the invention is preferably designed to be used to perform pipetting processes in accordance with a plurality of modes of operation of the pipetting apparatus. In one mode of operation, a particular set of operating parameters (operating parameter set) is preferably provided in each case, and is used to control a pipetting process which is performed in this mode of operation. Generally, an operating parameter set contains at least one operating parameter, and preferably, contains operating parameters, i.e. multiple operating parameters, i.e. at least two operating parameters. Respectively preferred, an operating parameter set contains at least three, or at least a number N4 of operating parameters, wherein, preferably, N4 is chosen from the range of numbers {2; 50}, or preferably from {2; 25}, or preferably from {2; 15}, or preferably from {2; 8}.

A pipetting process typically provides for a pipetting program to involve a particular quantity of sample being admitted from a starting container into a pipetting container that is connected to the pipetting apparatus and then being delivered back into a destination container, particularly being delivered in metered fashion. Depending on the application, the admission and/or delivery of the sample(s) can follow particular ordered patterns, particularly orders, of admission and delivery steps, can take place on the basis of time and can be attuned in terms of timing. A pipetting process can preferably be controlled by a set of operating parameters which can be used to influence the cited processes in the desired manner.

Operating parameters for controlling a pipetting process preferably relate to the selection of the volume to be pipetted, in the case of the step of the sample being aspirated into a pipetting container connected to the pipetting apparatus or in the case of the step of the sample being delivered from this pipetting container, possibly to the order and repetitions of these steps, and possibly to temporal parameters for the temporal distribution of these processes, particularly also to the alteration of such processes over time, particularly to the speed and/or acceleration of the sample being aspirated or delivered.

The pipetting process is preferably explicitly stipulated by the operating parameter set. This operating parameter set is preferably at least partially and preferably completely selected and/or input by the user, particularly using the operator control device of the pipetting apparatus.

However, it is possible for a pipetting process not to be explicitly stipulated by the operating parameter set. It is also possible and preferred for at least one operating parameter not to be stipulated by the user, but rather to be prescribed by the pipetting apparatus, for example, by virtue of its being stored therein, for example as previously known parameter(s). The pipetting apparatus may be designed to automatically determine at least one operating parameter.

By way of example, the pipetting apparatus may have a sensor device, for example a sensor for sensing an ambient parameter, particularly temperature, air humidity or pressure. The sensor device may also be designed to perform a measurement which can be used to ascertain the type of pipetting container that is connected to the pipetting apparatus, particularly the maximum filling volume of the pipetting container. The pipetting apparatus may be designed to determine at least one operating parameter automatically on the basis of the measured value from the sensor device.

Modes of operation and the operating parameters preferably associated therewith are described below, each preferably being provided for the pipetting apparatus:

Preferably, an operating parameter is provided which is used to define a pipetting volume to be pipetted. An operating parameter may be provided which is used to define an aspiration volume to be aspirated during an aspiration step, and/or an operating parameter may be provided which is used to define a delivery volume to be delivered during a delivery step.

Preferably, at least one operating parameter is provided which is used to stipulate the number of directly successive or indirectly successive pipetting volumes, preferably at least one operating parameter which is used to stipulate the number of aspiration steps and/or delivery steps and, in each case, preferably also the respective associated pipetting volumes, the respective associated pipetting speeds and/or accelerations, and/or the respective associated intervals of time between the steps.

Preferably, one mode of operation relates to the "Dispensing" (DIS) of a sample. Associated operating parameters are in each case preferably: the volume of the individual sample, relating to the pipetting volume during one of a plurality of delivery steps; the number of delivery steps; the speed at which the sample(s) is/are admitted; the speed at which the sample(s) is/are delivered. The dispensing function is particularly suitable for quickly filling a microtitre plate with a reagent liquid and can be used for performing an ELISA, for example.

Preferably, one mode of operation relates to the "Automatic dispensing" (ADS) of a sample. Associated operating parameters are in each case preferably: the volume of the individual sample, relating to the pipetting volume during one of a plurality of delivery steps; the number of delivery steps; the duration of the period according to which the delivery steps are automatically performed at constant intervals of time in succession—the period can stipulate these intervals of time or, by way of example, the delay between the end and the beginning of successive delivery steps; the speed at which the sample(s) is/are admitted; the speed at which the sample(s) is/are delivered. This dispensing function is even more conveniently suitable for filling a microtitre plate, since the user does not need to repeatedly initiate a delivery step by means of an operating action, e.g. pressing a key, but rather the delivered takes place under time control after the automatic dispensing is started. Like any other operating program in a mode of operation too, the automatic dispensing can take place under the condition that the relevant program is effected at least when an operating element is operated without interruption, e.g. when a key is held pressed without interruption. This is advantageous in the case of long dispensing operations or reactions, for example, in which precise attention to a time window is required. The automatic dispensing function is even more conveniently suitable for filling a microtitre plate, since the user does not need to initiate a single delivery step himself in this case, but rather this is done automatically, which can be used for performing an ELISA, for example.

Preferably, one mode of operation relates to the "Pipetting" (Pip) of a sample. Associated operating parameters are in each case preferably: the volume of the sample to be pipetted; the speed at which the sample is admitted; the speed at which the sample is delivered.

Preferably, one mode of operation relates to the "Pipetting with subsequent mixing" (P/Mix) of a sample. Associated operating parameters are in each case preferably: the volume of the sample to be aspirated and/or of the sample to be delivered; the mixing volume; the number of mixing cycles; the speed at which the sample is admitted; the speed at which the sample is delivered. The "Pipetting with subsequent mixing" function is recommended for pipetting very small volumes, for example. If a metering volume <10 µL is chosen, it is recommended that this be flushed into the respective reaction liquid. This is possible by virtue of the automatic starting of a mixing movement after the liquid has been delivered. The mixing volume and also the mixing cycles are defined beforehand. One application for this mode of operation is the delivery of a liquid which, on account of its physical properties, is more difficult than water to meter, for example, the residues of which in the pipetting container, particularly the pipette tip, are then rinsed out of the pipetting container, or the pipette tip, using the liquid that has already been presented. A further application would be the immediate mixing of the delivered liquid with the presented liquid. This mode of operation is advantageous when admixing DNA with a PCR mixed solution, for example.

Preferably, one mode of operation relates to the "Multiple admission" of a sample, also referred to as "Reverse dispensing" or as "ASP" for aspirating. Associated operating parameters are in each case preferably: the volume of the sample(s) to be aspirated; the number of samples; the speed of admission; the speed of delivery. The function is used for the multiple admission of a quantity of liquid and a delivery of the entire quantity. In this case, there is no provision for multiple filling of the pipetting container in one process. The speed is the same for all samples. The following preferably takes place during execution: starting from the basic position, the pipetting apparatus admits a respective partial volume as a result of a first type of operation of the operator control device. When the last partial volume has been admitted, the pipetting apparatus preferably outputs a warning message which preferably needs to be confirmed by the user by virtue of a second type of operation of the operator control device. When the operator control device is next operated in the second manner, the entire volume is delivered again. For operation of the first or second type, the operator control device preferably has at least two control buttons, one for inputting an operator control signal "of first type" into the control device, and one for inputting an operator control signal "of second type" into the control device. The operator control device may have a rocker, in particular, which can be pivoted about an axis perpendicular to the longitudinal axis of the pipetting apparatus, in particular, between a first signal initiation position "rocker up" for operation of the first type and a second signal initiation position "rocker down" for operation of the second type.

Preferably, one mode of operation relates to the "Diluting" (Dil) of a sample, also referred to as "dilution". Associated operating parameters are in each case preferably: the sample volume; the air bubble volume; the diluent volume; the speed of admission; the speed of delivery. The maximum diluent volume=nominal volume−(sample+air bubble). This function is used for the admission of a sample and of a diluent with separation by an air bubble and delivery of the entire quantity. The speed is the same for all partial volumes. The following preferably takes place during execution: starting from the basic position, the pipetting apparatus first of all admits the diluent volume, then the air bubble and finally the sample. Each admission is initiated preferably separately by means of operation of the operator control device of a first type. The entire quantity is then delivered in one.

Preferably, one mode of operation relates to the "Sequential dispensing" (SeqD) of samples. Associated operating parameters are in each case preferably: number of samples (preferably up to a firmly prescribed maximum number Nmax of preferably 5<=Nmax<=15, preferably Nmax=10); individual volumes of the individual samples; speed of admission; speed of delivery. This function is used for sequentially dispensing Nmax user-selectable volumes, in this case multiple filling of the pipetting containers is preferably not envisaged. The speed is the same for all samples. The number of samples is preferably the leading parameter for the input of the individual volumes. When the volumes are input, the pipette preferably always needs to check whether the maximum volume of the pipetting apparatuses is not exceeded; if appropriate, a warning message is output. When all the parameters have been input, the pipetting apparatus admits the entire volume when the operator control device has been operated in the first manner and delivers a respective individual volume when the operator control device has been operated in the second manner. All further cycles preferably behave in a manner of normal dispensing.

Preferably, one mode of operation relates to the "Sequential pipetting" (SeqP) of samples. Associated operating parameters are in each case preferably: number of samples (preferably up to a firmly prescribed maximum number Nmax of preferably 5<=Nmax<=15, preferably Nmax=10); individual volumes of the individual samples; speed of admission; speed of delivery. This function is used for pipetting a maximum of Nmax user-selectable volumes which are programmed before the start and have a fixed sequence. The speed is preferably the same for all samples in order to allow simple operator control of this mode of operation. Alternatively, the speed may be selectable in different ways. The cycle of the function corresponds to the cycle of pipetting. The previously input volumes are processed in the programmed order. Following delivery, operation of an operator control element, e.g. pressing a key, is used to decide whether the next sample is meant to be admitted or, before the next sample, a "blowout", that is to say complete, safe blowing-out of the sample which the pipetting container still contains first needs to be carried out by means of excess movement, and/or whether the pipetting container needs to be changed.

Preferably, one mode of operation relates to the "Reverse pipetting" (rPip) of samples. Associated operating parameters are in each case preferably: the volume of the individual sample; the speed of admission; the speed of delivery; activation of the counter. In the case of this "rPip" function, more than the volume to be metered is admitted. This is achieved by moving the piston downwards prior to the admission of liquid, namely by means of operation of the second type, i.e. by means of a key being pressed or "rocker downwards", for example, until it reaches the lower position for a blowout, that is to say for excess movement by the piston, which goes beyond the position of the piston during pipetting movement. At the start of the admission of volume, the pipetting apparatus admits the volume for the blowout and the selected volume. In order to remove the play in the propulsion in the delivery direction, the pipetting apparatus executes an additional movement which is immediately delivered again. This is similar to dispensing, but preferably takes place with automatic delivery of the rejection movement at maximum speed.

During execution of the "rPip" mode of operation, the following preferably takes place: first, the operator control device is operated in the second manner: the piston of the pipetting apparatus travels to blowout and remains stationary in the lower position. Secondly, the operator control device is operated in the first manner: the piston travels through the blowout section and through the movement for the pipetting volume upwards. Thirdly, the operator control device is operated in the second manner: the piston travels by the movement for the pipetting volume downwards and remains stationary before the blowout. Fourthly, the operator control device is operated in the second manner again: the piston performs the blowout and remains stationary in the lower position. As an alternative to "fourthly", the operator control device is operated in the first manner: the piston travels through the pipetting movement upwards. The "rPip" mode is particularly suitable for pipetting plasma, serums and other liquids having a high protein content. For aqueous solutions, the "Pipetting" mode is particularly suitable. The "rPip" mode is particularly suitable for solutions containing wetting agent in order to minimize the formation of foam upon delivery to the destination vessel. The liquid is admitted particularly with excess movement (blowout volume). In this case, the excess movement is typically not part of the delivery volume and is preferably not delivered to the destination vessel. Particularly when the same sample is used again, the excess movement can remain in the tip. When another liquid is used, the excess movement and/or preferably the pipetting container is/are preferably rejected.

An operating parameter set preferably controls a control program to perform the desired pipetting process. The control program may respectively be produced in the form of electric circuits of the control device, and/or may be produced by an executable program code which is suitable for controlling a control device which can be controlled by program code and is preferably programmable.

The pipetting apparatus is preferably designed to automatically check the parameter values that are input by the user and to compare them with a permitted range for the respective operating parameter. If the parameter value input by the user is outside the admissible range, the input is either not accepted or is set to a default value, which may be the minimum value or the maximum value or the last admissibly input value, for example.

Preferably, the electric control device is designed to perform the automatic storage of the parameter value set after the user has selected this parameter value set. Preferably, as an alternative or in addition to this condition, the electric control device is designed to perform the automatic storage of the parameter value set after the pipetting process has been performed completely at least once or precisely once. These conditions for the performance of the history function ensure particularly that each operating parameter set changed by the user is not stored unintentionally, but rather incorrectly input or rejected inputs are not included in the definition of the historic parameter value set, for example. This makes the use of the pipetting apparatus with a history function even more efficient.

Provision may also be made for the user to have to confirm the automatic storage of a parameter value set by operating an operator control element of the operator control device once. Apart from that, or preferably without this confirmation option, the automatic storage of a parameter value set particularly preferably takes place without further influence by the user. The minimal user interaction makes the use of the pipetting apparatus with a history function convenient and efficient.

Preferably, the pipetting apparatus is designed to prompt the memory device to be used to store at least one collection of a number N1 of historic parameter value sets with which the user is respectively provided and which the user can respectively select. In particular, this collection may be stored as a file or file constituent if the control device has a digital data processing installation, particularly a CPU and/or a data storage device. This collection is preferably associated with a particular mode of operation of the pipetting apparatus. Each parameter set of the collection is preferably used to perform a different pipetting process in the same mode of operation. This collection with historic parameter value sets can also be referred to as operating mode history. The number N1, preferably, is chosen from the range of numbers {1; 50}, or more preferably from {2; 50}, or preferably from {2; 25}, or preferably from {2; 15}, or preferably from {2; 8}. N1 can be larger than 50. Preferably, the number N1 is limited to be smaller than a maximum number L1, which defines an upper limit. This way, the user will not be confused by a too large number of historical sets of operating parameters, and the use of the pipetting apparatus is more comfortable. L1 is a number taken from the preferred ranges {5; 50}; {5; 25}; more preferred {5; 15}, or {8; 12}.

Preferably, the pipetting apparatus is designed to prompt a number N2 of collections of a number N1 of historic parameter value sets to be stored, wherein each collection of parameter value sets is associated with a particular mode of operation and wherein the user is respectively provided with a collection and the user can respectively select a parameter value set from this collection. The provision of an operating-mode-specific collection of historic parameter value sets makes the pipetting apparatus more convenient and more efficient to use. Preferably, the operating mode history of a mode of operation can be displayed by virtue of the user operating an operator control element of the operator control device a single time when the pipetting apparatus is in this mode of operation, so as preferably to subsequently allow the selection by virtue of the user operating an operator control element of the operator control device, particularly the same operator control element or preferably another operator control element, a further single time. The number N2, preferably, is chosen from the range of numbers {1; 50}, or more preferably from {2; 50}, or preferably from {2; 25}, or preferably from {2; 15}, or preferably from {2; 8}. N2 can be larger than 50. Preferably, the number N2 is limited to be smaller than a maximum number L2, which defines an upper limit. This way, the user will not be confused by a too large number of historical sets of operating parameters, and the use of the pipetting apparatus is more comfortable. L2 is a number taken from the preferred ranges {5; 50}; {5; 25}; more preferred {5; 15}, or {8; 12}.

Alternatively, it is possible for the collection of parameter value sets to be associated with more than a single mode of operation, particularly in a mixed operating mode history. The effect which can be achieved by this is that all, at least a number M, of most recently used pipetting processes can be made available to the user for fresh selection in a single, mixed collection.

The pipetting apparatus may be designed to provide user-dependent user profiles, with the history function being applied on a user-dependent basis, and at least one user-dependent operating mode history being automatically stored, under each user profile.

Preferably, the pipetting apparatus is designed to prompt individual historic parameter value sets, and/or the number N1 of historic parameter value sets and/or the number N2 of collections of a number N1 of historic parameter value sets, to be able to be additionally stored. This can preferably be accomplished under user control in each case by virtue of the user stipulating or initiating this. Alternatively, it can be performed semi-automatically or automatically, e.g. when a preferably provided backup function, particularly also called "history backup", is performed. The history backup involves the historic parameter value sets stored in the pipetting apparatus being stored in a backup memory, from which they can optionally be transferred to the pipetting apparatus again, this also being called "history restore". The backup memory may be an internal memory in the pipetting apparatus or may be external thereto, and may particularly be able to be connected by means of a wired or wireless data interface. In this way, it is possible to provide "historic" parameter value sets, or collections thereof, created by users or in the factory, for example, in order for them to be retrospectively transferred to the pipetting apparatus of a user. The user can then benefit directly from historic data from other users or from the factory without having created these functions himself. Such a function is advantageous particularly for pipetting processes in which a mode of operation is used by many users in the same way, e.g. for a standard procedure.

Preferably, the pipetting apparatus is designed to allow at least a single (or a plurality of or each) parameter from single historic parameter value sets, and/or the number N1 of historic parameter value sets and/or the number N2 of collections of a number N1 of historic parameter value sets, to be changed by the user and particularly to allow the data changed in this manner to be stored automatically or at the instigation of the user, or else not to be stored. This allows historic parameter value sets to be used more flexibly. After a parameter of a historic parameter value set has changed, if there is a collection of N1 historic parameter value sets from this mode of operation, there is preferably a change in the order in which particularly this number N1 of historic parameter value sets for a collection is displayed to the user and is made available for selection. The most recently changed historic parameter value set is preferably placed at the start of the collection of N1 parameter value sets, and preferably the oldest parameter value set is rejected from the collection.

Preferably, the pipetting apparatus has a display device which can be used to display the respective collection of historic parameter value sets to the user, and wherein a collection of historic parameter value sets is displayed to the user as an overview, particularly as a list, in each case at the request of the user (this function is referred to as "Display historic parameter value sets"), particularly is displayed as a result of operation of an operator control element on the operator control device, and wherein the pipetting apparatus is preferably designed to allow the user to select the desired parameter value set from this list and set it as an operating parameter set, which controls the pipetting process to be performed, preferably by means of single operation of the operator control device.

The display device is preferably a screen, preferably a colour display. The screen may have an input functionality, in particular it may be a touch screen.

Preferably, the operator control device has at least one operator control element having a variable function, which is also referred to as a softkey. An operator control element, particularly the softkey, may be particularly a programmable operator control element, the function of which can be programmed particularly by the user. Preferably, the softkey has an operating-mode-specific function which is dependent on the selected mode of operation of the pipetting apparatus.

Preferably, the pipetting apparatus has a display device and a plurality of at least partially predefined display pages which are stored in the pipetting apparatus and which can be displayed in the display device preferably so as to fill the screen, wherein the operator control element having a variable function has, on the basis of the displayed display page, a respectively predetermined function which is denoted and displayed on the display page preferably at a predetermined position. This function is—preferably in at least one, preferably in each, mode of operation of the pipetting apparatus and/or on at least one display page of the display device—the aforementioned function of the display of historic parameter value sets in the display device. This means that the history function is easily accessible to the user.

Preferably, the pipetting apparatus and/or the control device is/are designed to allow the function of the automatic storage of the historic parameter value set to be either activated and/or deactivated by the user.

Preferably, the softkey, preferably the at least one programmable operator control element, can be programmed by the user such that operation thereof either allows a collection of historic parameter value sets to be displayed to the user or allows at least one other piece of information to be displayed to the user, particularly help to explain the operating parameters of the mode of operation. As a result, the user himself can select whether he wishes to set up the pipetting apparatus for rapid access to the history function using this softkey or the programmable operator control element or whether he wishes to link a different function thereto. Preferably, the history function is not accessible when it has previously been deactivated by the user. Preferably, the history function is accessible when it has previously been activated by the user.

Preferably, the pipetting apparatus has a display device and a time recording device, wherein the number N1 of parameter value sets is sorted chronologically and in particular can be displayed in chronologically sorted form, wherein particularly the most recently stored historic parameter value set can be displayed at the first, particularly the topmost, position in a list. The time recording device may have a quartz oscillator. Preferably, the memory device is in the form of a FIFO memory (First In, First Out), which means that the data entered first are also rejected again first, particularly overwritten. The time recording device may be part of the control device, in particular.

Preferably, the pipetting apparatus has a counter device which can be used to count a number of recurring processes, e.g. the repeated delivery of a sample, the recurring aspiration of a sample or the recurring use of a mode of operation. The counter device is also referred to as a counter.

Preferably, the pipetting apparatus has a display device and a counting device, wherein the counting device respectively counts the number N3 of uses of a particular historic parameter value set and stores it in a memory device in the pipetting apparatus, wherein the number N1 of parameter value sets is sorted in accordance with the number N3 and, in particular, can be displayed in such sorted form, wherein particularly the historic parameter value set having the highest frequency N3 of use is displayed at the first, in particular the topmost, position in a list. The counting device may be implemented by a program code and/or may have electric circuits for implementing a counter. The counting device may be part of the control device, in particular. N3 can be a number, depending on the counting status, larger or equal than one.

The inventive method for operating an electric pipetting apparatus, particularly the inventive pipetting apparatus, to control a pipetting process on at least one fluid laboratory sample in accordance with at least one mode of operation of the pipetting apparatus, which has an electric control device and an operator control device, preferably has the following steps:
  an operating parameter set is stipulated by the user of the pipetting apparatus, wherein the operating parameter set is associated with a mode of operation and respectively comprises at least one operating parameter, wherein the user stipulates the operating parameter by selecting the desired value of the operating parameter as a parameter value and in this way determining a parameter value set having at least one parameter value;
  the at least one parameter value set which is determined by the user, and which is associated with the operating parameter set for a mode of operation, is automatically stored as the at least one historic parameter value set for this mode of operation in an electric memory device in the pipetting apparatus;
  after the operating parameter set for this mode of operation has changed: the at least one automatically stored historic parameter value set for this mode of operation is provided again for the subsequent control of the at least one, same, pipetting process.

Further preferred refinements of the method according to the invention can be found in the description of the pipetting apparatus and the preferred refinements thereof.

Further preferred refinements of the pipetting apparatus according to the invention and of the method according to the invention can also be found in the description of the exemplary embodiments below in conjunction with the figures and the description thereof. Identical components of the exemplary embodiments are essentially denoted by the same reference symbols unless a different description is given for this or the context reveals otherwise. In the figures:

FIG. 3b shows the "Option history" display page from FIG. 3a, the history function being switched on.

FIG. 5b shows the "Special" display page from FIG. 5a, the history function being switched on.

Figure 1:
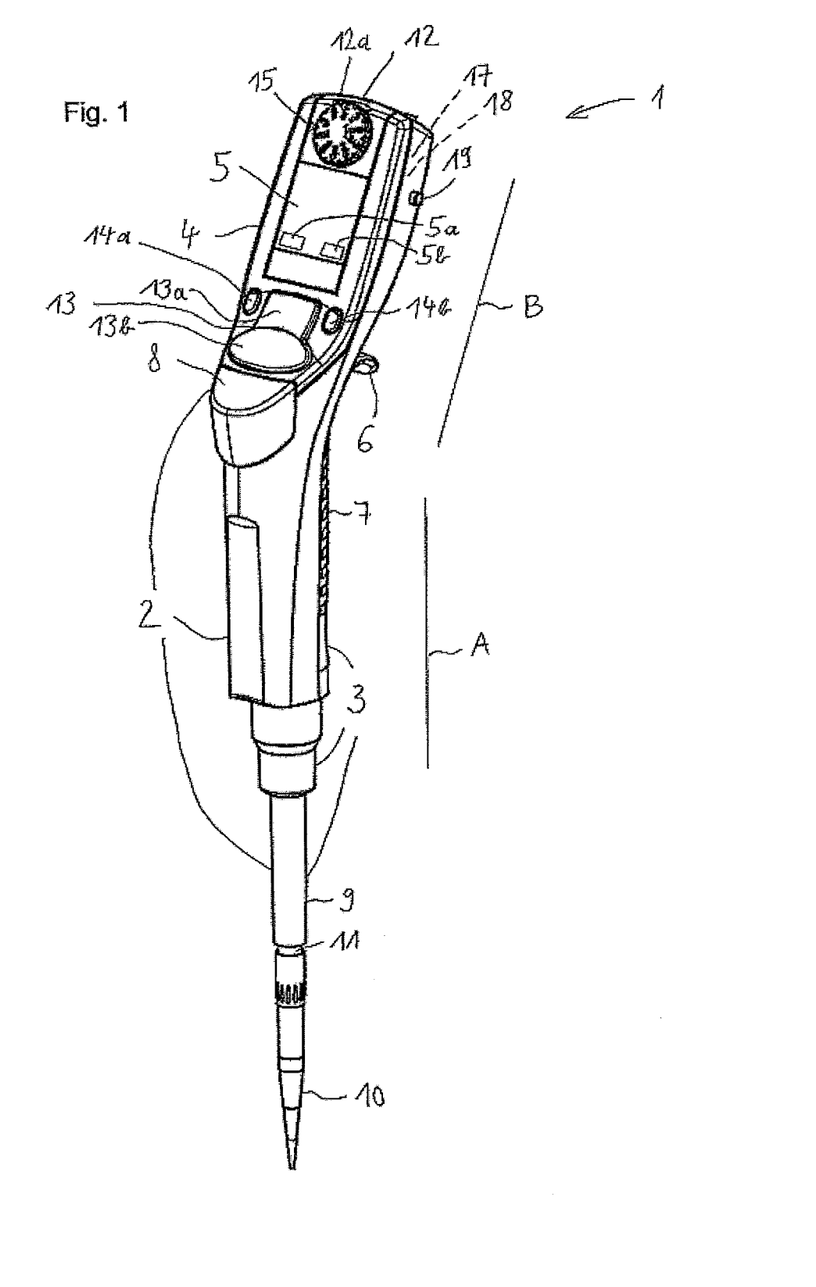
FIG. 1 shows a perspective view of a first exemplary embodiment of the pipetting apparatus according to the invention.

FIG. 1 shows a perspective view of the pipetting apparatus 1, an electric pipette 1. In the electric pipette 1, the movement of the piston is driven electrically. The actuation of the movement in the various modes of operation of the pipette is electrically controlled by an electric control device 17 having a connected memory device 18, in this case a FLASH memory, inside the pipette 1. The FLASH memory allows at least 150 000 write cycles, which means that the history function of the pipette can be performed particularly reliably over the plurality of years of life of the pipette.

The operating parameters and other selections for the pipette can be controlled by the user by means of the operator control device and the display of the pipette. The pipette stores a plurality of electrically controlled pipetting programs, each mode of operation preferably having an associated pipetting program. A pipetting program can be explicitly stipulated by an operating parameter set. Once stipulated, the pipetting program can be initiated by the user and is automatically started by the pipetting apparatus.

The pipette 1 has a basic body 2 which has a lower shaft section 3 and an upper section 4, which has the display 5 and operator control elements, in particular. The shaft section 3 extends parallel to the longitudinal axis A of the pipetting apparatus, while the upper section 4 is arranged at an inclination with respect to the axis A and extends parallel to the axis B. The inclined arrangement of the upper section 4 allows the display 5 to be used particularly ergonomically.

The pipette 1 has a grip area 7 having the holding tongue 6, which, when the user is holding the pipette 1 as intended, is supported on the index finger of the user, while the grip area 7 rests in the palm of the user. The thumb is able to reach particularly the release button 8, which, when pushed downwards along the axis A, moves the spring-mounted release sleeve 9 downwards and prompts it to release the pipette tip 10 from the connecting cone 11 of the pipetting apparatus, on which it is fitted. Alternatively, the release mechanism can be driven electronically. The lateral faces of the upper section 4 of the pipette 1 each have a metal contact projection 19 which is used for charging the integrated storage battery which forms the energy store for the electric pipette.

The operator control device (12; 13; 14*a*; 14*b*) has a selector wheel 12, a rocker 13 and a first control button 14*a* and a second control button 14*b*.

The disk-like selector wheel 12 is mounted rotatably on the basic body 2, in particular parallel to the essentially planar front of the upper section 4. A device for recognizing the position of the selector wheel 12 is provided, which in the present case has a Hall sensor, which is used to contactlessly measure the relative position of the selector wheel 12 relative to the basic body. The selector wheel 12 has a number of detents which correspond to the number of selectable positions for the selector wheel. In particular, the detents are such that a marker 12*a* for denoting the selected position of the selector wheel 12 can be oriented to the marker 15, which is arranged permanently on the basic body 2 on the front of the upper section 4.

The colour display 5 is used as a central information element for the user. It displays particularly the various modes of operation of the pipette 1 and displays the parameter values of the operating parameters. The two areas 5*a* and 5*b* each display a piece of information which tells the user which function on the currently displayed display page is linked to the first control button 14*a* or the second control button 14*b* if the respective display page also contains a function that is linked thereto. Each of the control buttons is therefore in the form of an operator control element having a variable function and, in combination with its displayed function, is referred to as a "softkey". This will be explained below.

Preferably, the pipetting apparatus is designed to alternate between the various functions of a softkey when a particular mode of operation of the pipetting apparatus is selected. By way of example, this can be achieved by double-clicking on the softkey or pressing the softkey for longer for a minimum period, for example 2 seconds.

Preferably, a display page which is presented on the display and which has an operating-mode-specific layout is provided for each mode of operation of the pipette 1. If selectable operating parameters or other entries which can be changed are provided on the display page, they can be marked using the control rocker 13 and can be selected using the control button 14*a*, in particular, in which case the control button 14*a* has the "Select" function and the text "Select" is displayed in the display at the position 5*a*. The parameter values of an operating parameter are changed, or a selection or an entry is changed, by operating the rocker 13.

The rocker 13 is arranged on the basic body so as to be swivelable about a swivel axis arranged perpendicular to the longitudinal axis A. When the user pushes the upper area 13*a*, a first function of the rocker 13 is activated, and when the user pushes the lower area 13*b*, a second function of the rocker 13 is activated. The rocker is mounted such that no function is initiated when it is not being operated. The rocker 13 is used particularly in the manual mode of operation of the pipette for aspirating the sample to be pipetted into the pipette tip 10 while the upper area 13*a* is being pushed by the user, and is also used to deliver the sample from the pipette tip 10 while the lower area 13*b* is being pushed by the user.

The pipette 1 can be operated in various modes of operation, which have already been explained in detail previously. A first number of modes of operation can be selected directly by means of the selector wheel 12, and a second number of modes of operation can be selected by means of a display page, which is denoted by "Special" or "Spc", having a plurality of selectable entries, each entry describing a mode of operation.

The pipette 1 has a history function which can be activated by the user. This means that when the history function of the pipette is activated an operating-mode-specific operating-mode history is created for each mode of operation. The relevant softkey, in this case 14*b*/5*b*, can usually be used by the user to call the operating-mode history when the operating-mode-specific display page is displayed.

The pipette 1 has a memory device which contains suitable memory areas for the operating-mode histories.

Figure 2A:
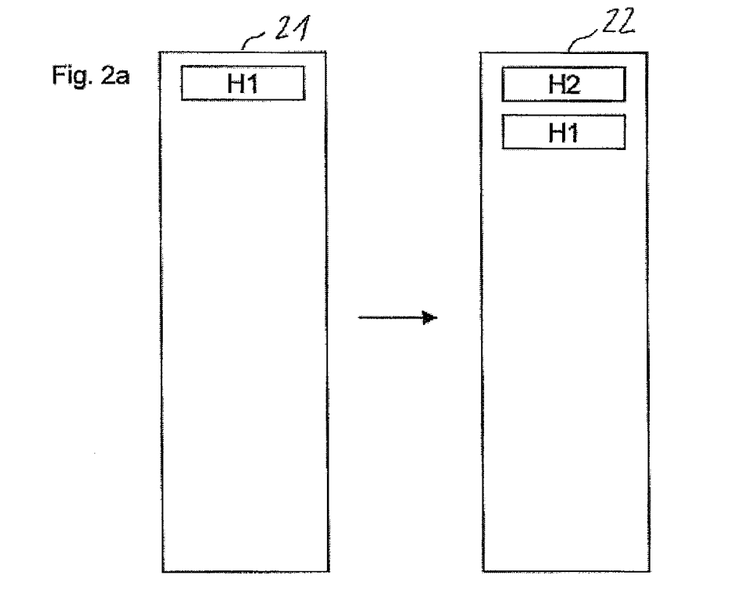
FIG. 2a schematically shows a memory area of the memory device in the pipetting apparatus from FIG. 1, in a first state and in a second state.

FIG. 2*a* schematically shows a memory area of the memory device 18 in the pipetting apparatus from FIG. 1, in a first state and in a second state. A memory area is suitable for storing a maximum number Nmax=10—stipulated by the appliance—of entries, with an entry corresponding to a parameter value set in line with the operating parameter set of a mode of operation. FIG. 2*a* relates to the case in which the memory area is still not full to the maximum level, since the number of maximum possible entries in the memory area has not yet been reached. This is always the case in the period in which the pipette is used for the first time, for example. The box 21 represents the memory area in the first state, and the box 22 represents the memory area in the second state.

The pipette 1 automatically stores a parameter value set when it has been stipulated by the user by means of the relevant selections on the display page of the mode of operation (1st condition) and when afterwards the user has performed the pipetting process completely with this parameter value set (2nd condition). If one of the two conditions is not met, the parameter value set stipulated by the user is not entered in the operating-mode history.

In the first state 21 in FIG. 2*a*, there is precisely one entry "H1" in the operating-mode history in the memory area. In the second state 22 in FIG. 2*a*, there are precisely two entries "H2" and "H1" in the operating-mode history in the memory area. The entry H1 represents a first parameter value set for this mode of operation, and the entry H2 represents a second parameter value set for this mode of operation, H1 and H2 differing in at least one parameter value, that is to say in at least one operating parameter. The entries for the operating-mode history are arranged in chronologically sorted form, with the most recent entry being displayed right at the top. When a new entry is made, the previous entries each automatically move one level downwards. Once the maximum number of entries is reached, the memory area preferably works in the manner of a FIFO memory: the oldest entry is erased from the list and the new entry occupies the first position, while the other nine entries automatically move one level downwards. This case is shown in FIG. 2b.

Figure 2B:
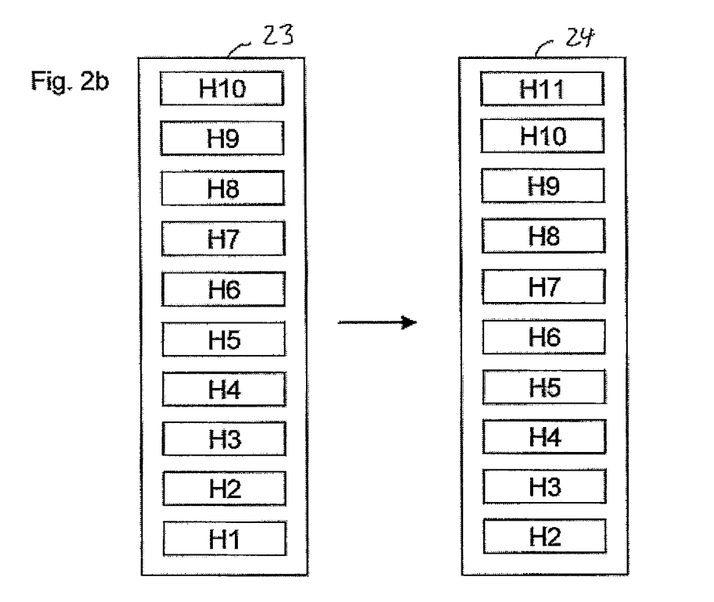
FIG. 2b schematically shows a memory area of the memory device in a pipetting apparatus from FIG. 1, in a third state and in a fourth state.

FIG. 2b schematically shows a memory area of the memory device in the pipetting apparatus from FIG. 1, in a third state 23 and in a fourth state 24. In the third state 23, the memory area is completely filled with entries, H10 being the most recent entry and H1 being the oldest entry. When a new entry is automatically entered, the oldest entry H1 is automatically erased, the new entry occupies the first position and the previous entries H9 to H2 automatically move one level downwards. It is not the case here, but there is preferably provision made, that the list of the operating-mode history is sorted at least partially on the basis of the frequency with which a particular entry is used, that is to say the number of times a pipetting process is performed with the parameter value set. This frequency may relate particularly to a limited period of use of the pipetting apparatus or to the entire period of use of the pipetting apparatus.

Figure 3A:
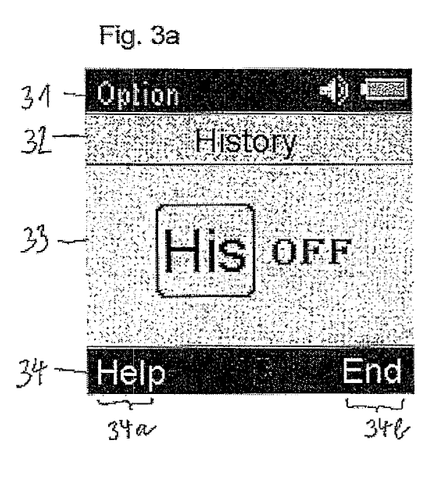
FIG. 3a shows a display page from a plurality of possible display pages which are displayed on the display of the pipetting apparatus from FIG. 1, namely the "Option history" display page, the history function being switched off.

FIG. 3a shows a display page from a plurality of possible display pages which are displayed on the display of the pipetting apparatus from FIG. 1, namely the "Option history" display page, the history function being switched off. The "Option history" display page shown can be reached by means of the selector wheel 12 and the "Opt" position and by subsequently selecting it from a list of options using the rocker 13 and operating the control button 14a to which "Select" is assigned. The display page has an upper first title bar 31, an upper second title bar 32, a larger, central information box 33 and a lower bar 34, which states particularly the functions 34a and 34b which are currently assigned to the two softkeys 14a and 14b on the basis of this display page. The upper title bar 31 is used to display whether—and/or at what volume—the integrated loudspeaker of the pipette, which is used particularly for outputting warning signals and other signals to the user, is in operation, for example. The upper title bar 31 also indicates the battery charge state.

Figure 3B:
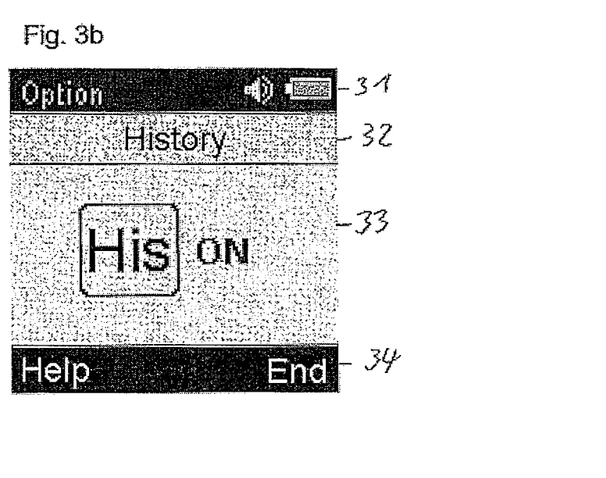

When this "Option history" display page is displayed in the display 5, the text "Help" is shown in the area 5a of the display 5, and the text "End" is shown in the area 5b of the display 5. By operating the rocker 13, the user can alternate between a first state of the pipette, in which the history function is deactivated ("His off"; FIG. 3a), and a second state of the pipette, in which the history function is activated ("His on"; FIG. 3b). By operating the softkey 14b with the current "End" function, the user returns to the display page (not shown here) of the option menu.

When the user has activated the history function of the pipette 1 in this manner, he has in this way simultaneously programmed the function of the softkey 14b such that the operating-mode-specific display page respectively holds the entry 34b "History", which means that the user respectively reaches the relevant operating-mode-specific display page of the operating-mode history starting from this display page by means of the softkey 14b. If the history function is deactivated, the softkey 14b preferably has the assigned function "Help" as standard on the operating-mode-specific display page, the user using said function to respectively obtain a display page with explanations of the operating parameters of the relevant mode of operation. In this sense, the softkeys 14a and 14b are each an operator control element which can be programmed by the user.

Figure 4A:
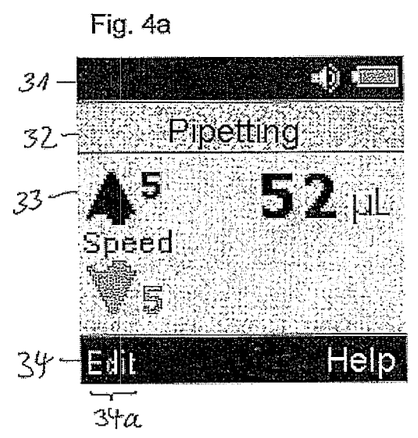
FIG. 4a shows a display page which is displayed on the display of the pipetting apparatus from FIG. 1 when the "Pipetting" mode of operation of the pipetting apparatus is selected and the history function is deactivated.

FIG. 4a shows an operating-mode-specific display page which is displayed on the display of the pipetting apparatus from FIG. 1 when the "Pipetting" mode of operation of the pipetting apparatus is selected and the history function is deactivated. The function of the softkey 14a is "Edit", which allows the selectable boxes in the display page to be selected (optional "Select" function of the softkey 14a) and to be adjusted by means of the rocker 13.

Figure 4B:
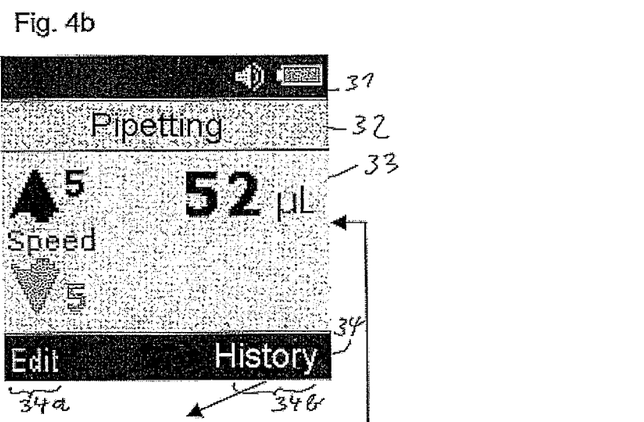
FIG. 4b shows a display page which is displayed on the display of the pipetting apparatus from FIG. 1 when the "Pipetting" mode of operation of the pipetting apparatus is selected and the history function is activated.

FIG. 4b shows an operating-mode-specific display page which is displayed on the display of the pipetting apparatus from FIG. 1 when the "Pipetting" mode of operation of the pipetting apparatus is selected and the history function is activated.

Figure 4C:
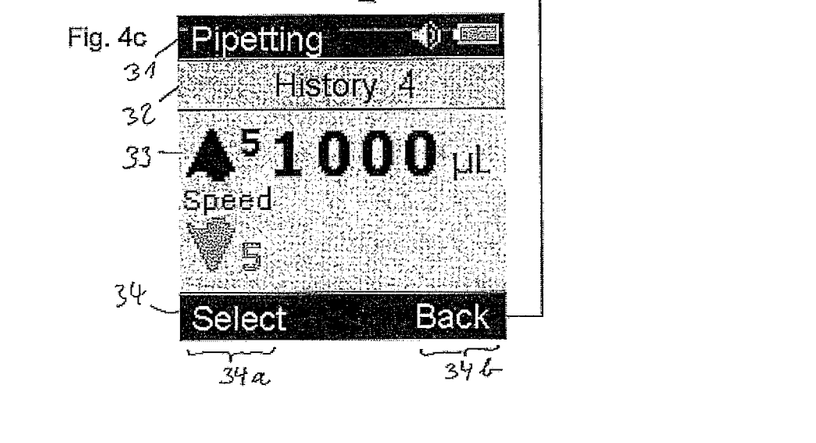
FIG. 4c shows a display page from the operating-mode history of the "Pipetting" mode of operation which is displayed on the display of the pipetting apparatus from FIG. 1 when the "Pipetting" mode of operation of the pipetting apparatus is selected and the operating-mode history has been called by the user.

FIG. 4c shows an operating-mode-specific display page of the operating-mode history for the "Pipetting" mode of operation which is displayed on the display of the pipetting apparatus from FIG. 1 when the "Pipetting" mode of operation of the pipetting apparatus is selected and the operating-mode history has been called by the user, this being symbolized by an arrow from FIG. 4b to FIG. 4c. In the upper second title bar 32, the information "History 4" is displayed, which represents that entry from the operating-mode history which is at the fourth position in the list counting from the top, that is to say the fourth most recent entry in the operating-mode history. Operating the rocker 13 on this display page alternates in steps between the—in this case—maximum of ten entries in the operating-mode history. Operating the softkey 14a selects the relevant parameter value set and changes back to the operating-mode-specific display page again (in similar fashion to FIG. 4b), which then shows the parameter values from the relevant parameter value set, however. The subsequent pipetting process then uses this parameter value set.

Figure 5A:
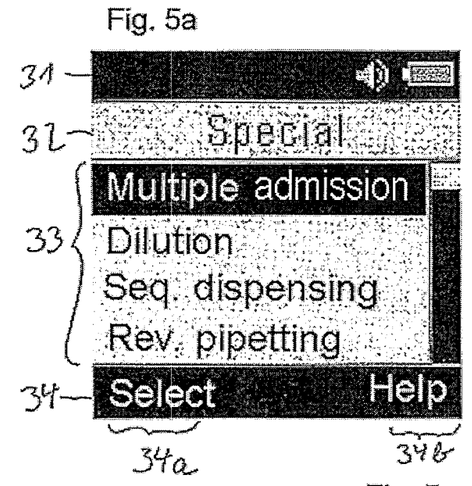
FIG. 5a shows a display page from a plurality of possible display pages which are displayed on the display of the pipetting apparatus from FIG. 1, namely the "Special" display page, the history function being switched off.

FIG. 5a shows an operating-mode-specific display page from a plurality of possible display pages which are displayed on the display of the pipetting apparatus from FIG. 1, namely the "Special" display page, the history function being switched off. This display page can be used to select a second number of modes of operation. In particular, this display page can be used to directly call the operating-mode history associated with the respective mode of operation using the softkey 14b "History", if the history function is activated. Otherwise, position 34b in the lower bar 34 offers the help function, which the user uses to obtain explanations regarding the operating parameters of the selected mode of operation.

Figure 5B:
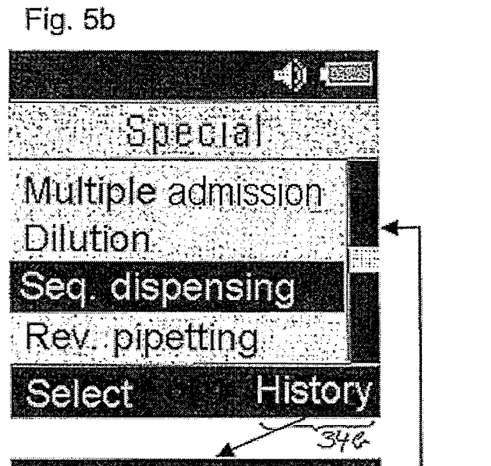

FIG. 5b shows the "Special" display page from FIG. 5a, the history function being switched on.

Figure 5C:
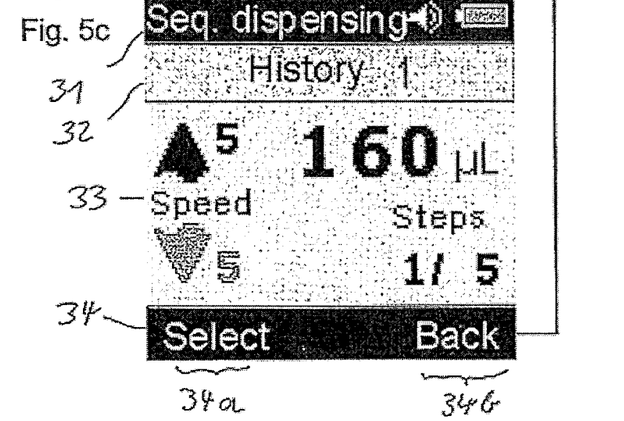
FIG. 5c shows a display page from the operating-mode history of the "Seq. dispensing" mode of operation which is displayed on the display of the pipetting apparatus from FIG. 1 when the "Seq. dispensing" mode of operation of the pipetting apparatus is selected and the operating-mode history has been called by the user.

FIG. 5c shows an operating-mode-specific display page for the operating-mode history of the "Seq. dispensing" mode of operation which is displayed on the display of the pipetting apparatus from FIG. 1 when the "Seq. dispensing" mode of operation of the pipetting apparatus is selected and the operating-mode history has been called by the user. In the upper second title bar 32, the information "History 1" is displayed, which represents that entry from the operating-mode history which is at the first position in the list counting from the top, that is to say the most recent entry in the operating-mode history. Operating the rocker 13 on this display page alternates in steps between the—in this case—maximum of ten entries in the operating-mode history. Operating the softkey 14a selects the relevant parameter value set and changes back to the operating-mode-specific display page again (in similar fashion to FIG. 5b), which then shows the parameter values from the relevant parameter value set, however. The subsequent pipetting process then uses this parameter value set.

The history function option automatically provides the user with the previously used parameter value sets in a convenient manner. A desired pipetting process which follows a pipetting program based on the operating parameter set stipulated in this manner can thus be conveniently selected. Thus, the user saves numerous editing steps, in particular, which are required particularly when he creates, names and stores an individual pipetting program by means of programming. This option is provided for the pipette 1 additionally and independently of the history function. Furthermore, the user preferably also has the option of changing the individual parameters as required following the selection and setting of a particular parameter value set for the operating parameter set. As soon as the pipetting program has been performed once on the basis of the historic parameter value set changed in this manner, the historic parameter value set changed in this manner is stored as a new historic parameter value set.

The invention claimed is:

1. Pipetting apparatus (1), for performing an at least partially electrically controlled pipetting process on at least one fluid laboratory sample in accordance with at least one mode of operation of the pipetting apparatus, having
    an electric control device (17) for controlling the pipetting process, said control device being able to be controlled by an operating parameter set which is used to control the pipetting process, which is able to be stipulated by a user and which is associated with a mode of operation and respectively comprises at least two operating parameters for controlling the pipetting process, wherein the user stipulates the at least two operating parameters by selecting the desired values of the at least two operating parameters as the parameter values and in this way determining a parameter value set having at least two parameter values,
    at least one operator control device (12, 13, 14*a*, 14*b*) for the stipulation of the operating parameter set by the user,
    an electric memory device (18) for storing the at least one parameter value set,
characterized in that
the electric control device (17) is designed to automatically store the at least one parameter value set determined by the user as the at least one historic parameter value set for this mode of operation in the memory device (18);
wherein the electric control device is designed to perform the automatic storage of the parameter value set without any further influence by the user after the user has selected this parameter value set; and
wherein the electric control device is designed to provide again from the electric memory device (18), after the operating parameter set for this mode of operation has changed, the at least one automatically stored historic parameter value set for this mode of operation for the subsequent control of the at least one, same, pipetting process.

2. Pipetting apparatus according to claim 1, wherein the electric control device is designed to perform the automatic storage of the parameter value set without any further influence by the user after the pipetting process using said parameter value set has been performed completely at least once.

3. Pipetting apparatus according to claim 1, wherein the memory device is used to store at least one collection of a number N1 of historic parameter value sets with which the user is respectively provided and which the user can respectively select.

4. Pipetting apparatus according to claim 3, wherein the pipetting apparatus is designed to prompt a number N2 of collections of a number N1 of historic parameter value sets to be stored, wherein each collection of parameter value sets is associated with a particular mode of operation and wherein the user is respectively provided with a collection and the user can respectively select a parameter value set from this collection.

5. Pipetting apparatus according to claim 3 or 4 which has a display device (5) on which the respective collection of historic parameter value sets can be displayed to the user, and wherein a collection of historic parameter value sets is displayed to the user as an overview at the respective request of the user by virtue of the operation of an operator control element of the operator control device, and wherein the pipetting apparatus is designed to allow the user to select the desired parameter value sets from this overview and to set it as an operating parameter set by means of a single operation of the operator control device.

6. Pipetting apparatus according to claim 1, wherein the operator control device has at least one operator control element having a variable function, the operator control element being a programmable operator control element, the function of which can be programmed.

7. Pipetting apparatus according to claim 6, which has a display device (5) and can display a multiplicity of at least partially predefined display pages stored in the pipetting apparatus, wherein the operator control element having a variable function has a respective predetermined function on the basis of the displayed display page.

8. Pipetting apparatus according to claim 6, wherein the function of the at least one operator control element having a variable function is the function of the display of historic parameter value sets in the display device.

9. Pipetting apparatus according to claim 6, wherein the at least one programmable operator control element can be programmed by the user such that operation of said operator control element can either display a collection of historic parameter value sets to the user or can display at least one other piece of information to the user.

10. Pipetting apparatus according to claim 1, wherein the pipetting apparatus and/or the control device is/are designed to allow the function of the automatic storage of the historic parameter value sets to be either activated and/or deactivated by the user.

11. Pipetting apparatus according to claim 3, which has a display device (5) and a time recording device, wherein the number N1 of parameter value sets is sorted chronologically and is displayed in chronologically sorted form, wherein the most recently stored historic parameter value set is displayed at the first position in a list.

12. Pipetting apparatus according to claim 3, which has a display device and a counting device, wherein the counting device respectively counts the number N3 of uses of a particular historic parameter value sets and stores it in a memory device in the pipetting apparatus, wherein the number N1 of parameter value sets is sorted in accordance with the number N3.

13. Method for operating an electric pipetting apparatus (1), to control a pipetting process on at least one fluid laboratory sample in accordance with at least one mode of operation of the pipetting apparatus, which has an electric control device and an operator control device, having the following steps:
    an operating parameter set is stipulated by the user of the pipetting apparatus by the operator control device, wherein the operating parameter set is associated with a mode of operation and is used to control the pipetting process, and wherein the operating parameter set respectively comprises at least two operating parameters for controlling the pipetting process, wherein the user stipulates the at least two operating parameters by selecting the desired values of the at least two operating parameters as the parameter values and in this way determining a parameter value set having at least two parameter values;
    the at least one parameter value set which is determined by the user, and which is associated with the operating parameter set for a mode of operation, is automatically stored without further influence of the user as the at least one historic parameter value set for this mode of operation in an electric memory device in the pipetting apparatus;

after the operating parameter set for this mode of operation has changed: the at least one automatically stored historic parameter value set for this mode of operation is provided again from the electric memory device by the electric control device for the subsequent control of the at least one, same, pipetting process;

wherein said steps are carried out within the pipette itself.

14. The method of claim 13 for operating an electric pipetting apparatus, which has a display device and a plurality of at least partially predefined display pages which are stored in the pipetting apparatus and which can be displayed in the display device, and has an operator control device having at least one operator control element, wherein the at least one historic parameter value set for this mode of operation is referred to as operating mode history and the pipetting apparatus is configured to have the operating mode history be called by the user by virtue of the user operating an operator control element of the operator control device, the method comprising the further steps:

displaying a display page on the display of the pipetting apparatus;

letting the user call the operating-mode history starting from said display page by virtue of the user operating an operator control element; and displaying, upon operating the operator control element, another display page of the operating mode history on the display of the pipetting apparatus, to subsequently allow the selection of a historic parameter value set from the operating mode history by virtue of the user operating an operator control element of the operator control device.

15. Pipetting apparatus according to claim 1 or 2, wherein the pipetting apparatus has a display device and a plurality of at least partially predefined display pages, which are stored in the pipetting apparatus and which can be displayed in the display device, and the operator control device has at least one operator control element, wherein the at least one historic parameter value set for this mode of operation is referred to as operating mode history and the pipetting apparatus is configured to have the operating mode history be called by the user by virtue of the user operating an operator control element of the operator control device, wherein the pipetting apparatus is configured to display a display page on the display of the pipetting apparatus and the pipetting apparatus is configured to let the user call the operating-mode history starting from said display page, and wherein the pipetting apparatus is configured to display, upon operating the operator control element, another display page of the operating mode history, which is displayed on the display of the pipetting apparatus when the operating-mode history has been called by the user, to subsequently allow the selection of a historic parameter value set from the operating mode history by virtue of the user operating an operator control element of the operator control device.

16. Pipetting apparatus according to claim 1, wherein the electric memory device further comprises at least one memory area, which can be addressed by the electric control device, wherein the at least one memory area is suitable for storing entries, with an entry corresponding to a parameter value set, and wherein the at least one historic parameter value set is stored as an entry in the at least one memory area.

* * * * *